United States Patent [19]

Eggertsen

[11] 4,366,710

[45] Jan. 4, 1983

[54] METHOD FOR MEASURING VAPOR PRESSURE

[75] Inventor: Frank T. Eggertsen, Berkeley, Calif.

[73] Assignee: Flint Ink Corporation, Detroit, Mich.

[21] Appl. No.: 246,078

[22] Filed: Mar. 20, 1981

[51] Int. Cl.$^3$ .............................................. G01N 31/08
[52] U.S. Cl. ..................................................... 73/23.1
[58] Field of Search .......................... 73/23.1; 422/89; 364/498

[56] References Cited

U.S. PATENT DOCUMENTS 3,527,926 9/1970 Holy ..................................... 73/23.1
3,550,428 12/1970 Mator et al. .......................... 73/23.1

*Primary Examiner*—Stephen A. Kreitman

*Attorney, Agent, or Firm*—Manfred M. Warren; Robert B. Chickering; Glen R. Grunewald

[57] ABSTRACT

Determining saturation vapor pressure of a hydrocarbon mixture by chromatographic analysis of the mixture, recording n-paraffin positions on said analysis establishing n-paraffin bisectors halfway between n-paraffin positions, determining the number of moles of compounds represented between n-paraffin bisectors by assigning the C-number of the n-paraffin between bisectors to all compounds between bisectors, determining the mole fraction of compounds between each pair of n-paraffin bisectors, determining the partial pressure of the compounds between n-paraffin bisectors by assigning to that mole fraction the saturation vapor pressure of the n-paraffin, and adding all partial pressures thus obtained.

7 Claims, 5 Drawing Figures

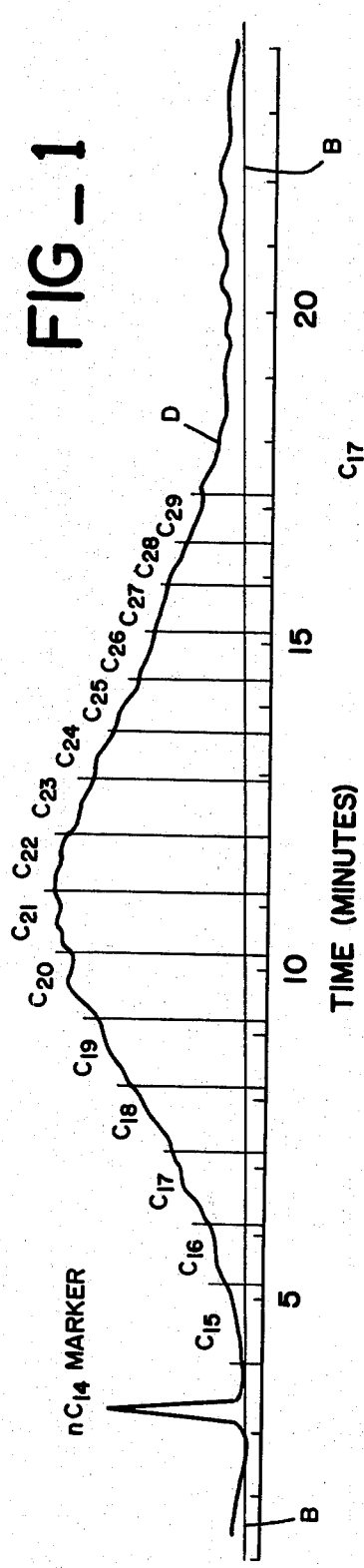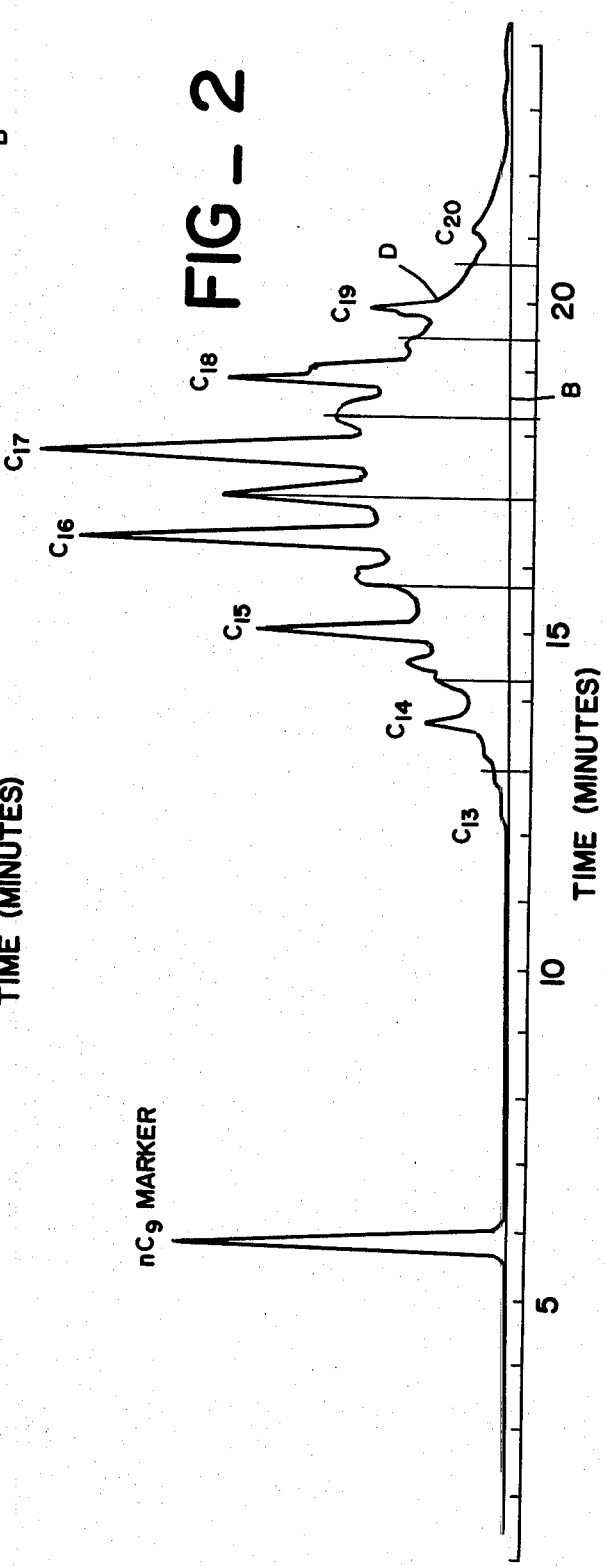

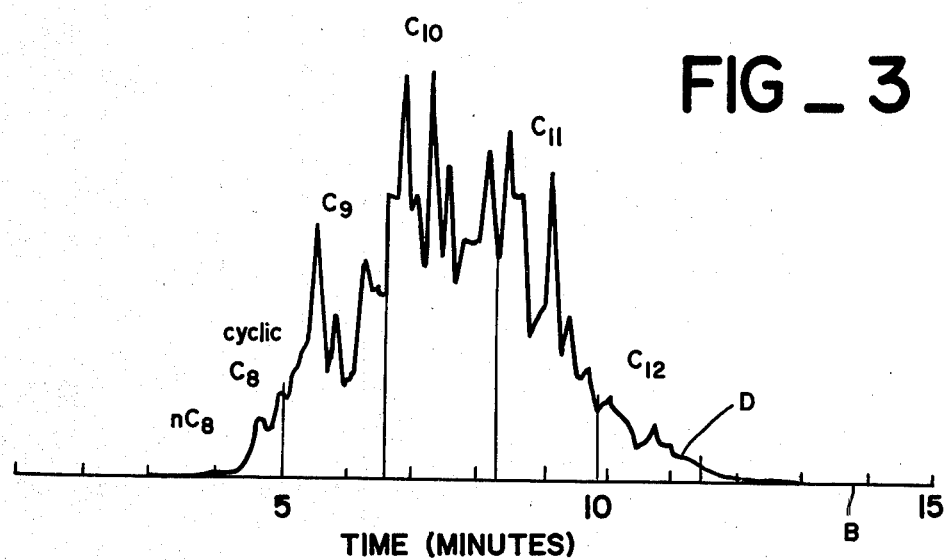
FIG_3
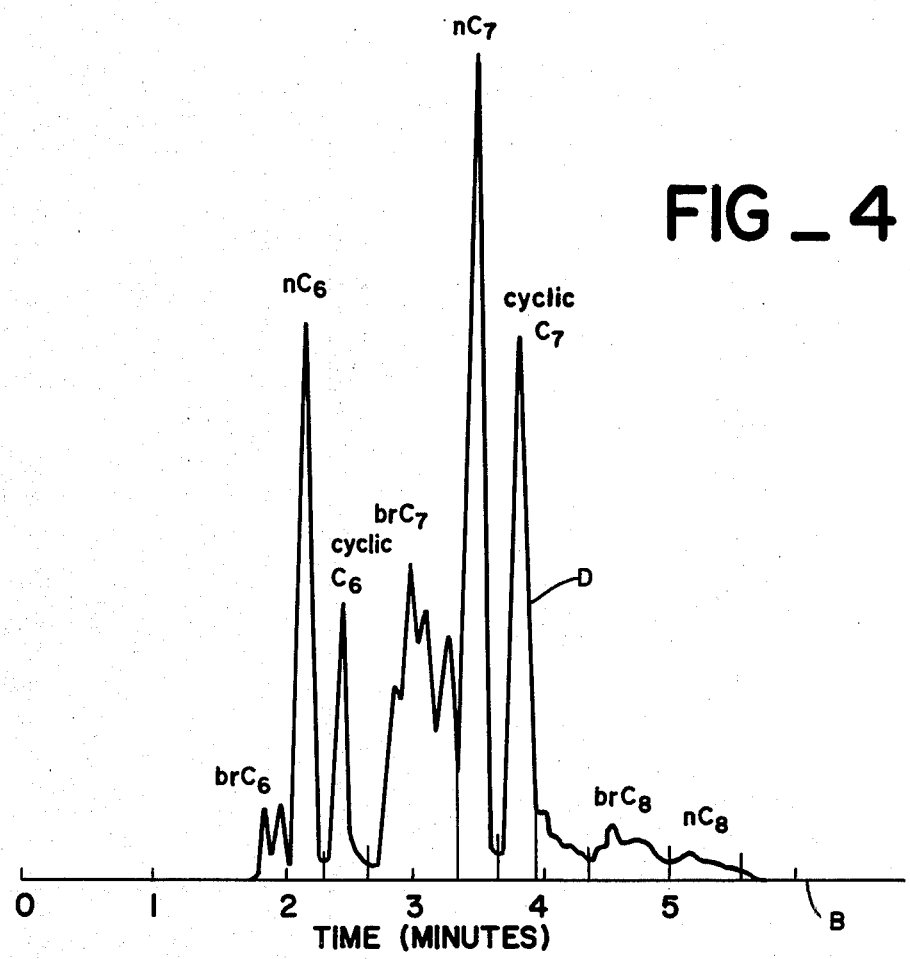
FIG_4

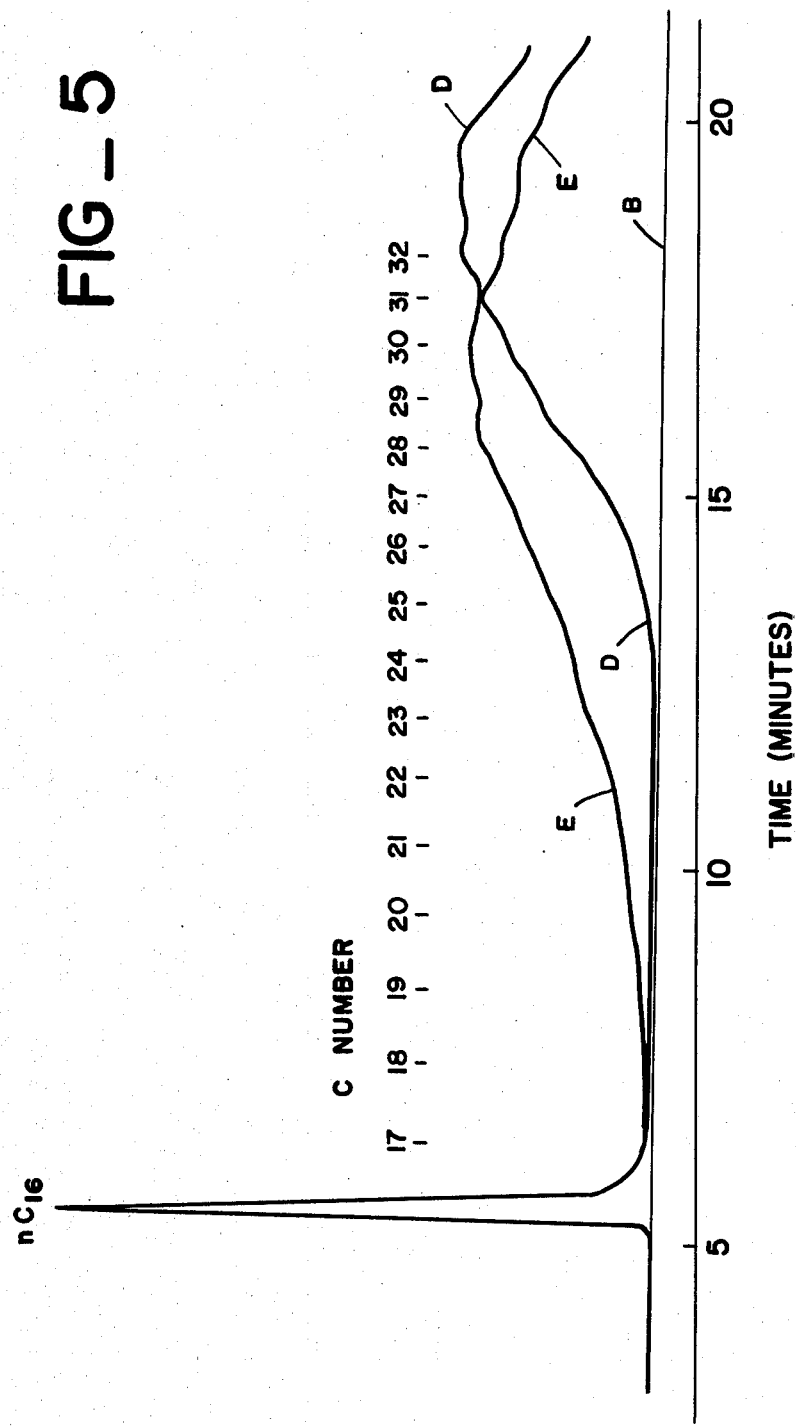

METHOD FOR MEASURING VAPOR PRESSURE

BACKGROUND OF THE INVENTION

It is frequently desirable to know the volatility of a material. One measure of volatility is vapor pressure, which is defined as the pressure at which a liquid and its vapor are in equilibrium at a given temperature. Higher vapor pressure indicates greater volatility.

It is desirable to know the volatility of a material for many reasons. Among these are to predict the degree to which a material will pollute the air. The vapor pressure of a material also corresponds to the danger to workers caused by inhaling fumes of that material. The flammability of a material also corresponds to its vapor pressure as well as the ability of a material to dry, or skin over. Many products have vapor pressure specifications and determining the vapor pressure of these products is required for quality control.

Many materials do not have a significant vapor pressure at room temperature but will have a high vapor pressure at elevated temperatures. For example, roofing tars neither pollute the air nor endanger workers who work with them when they are cool and installed on a roof but the ability of these tars to pollute the air, endanger workers, or burst into flames is significant at the high temperatures at which they are maintained when they are being installed. The vapor pressure of roofing tar also corresponds to how rapidly flame spreads in a fire.

Measuring vapor pressure is a difficult and time consuming process that frequently requires a skilled analyst. Even measuring the vapor pressure of relatively volatile materials, such as gasoline, requires establishing equilibrium conditions between the liquid and the gas and then making the delicate measurements necessary to determine the vapor pressure of the material. Measuring the vapor pressure of materials having low volatility is extremely difficult because the vapor in equilibrium with the material is at such low concentration. Known methods for measuring vapor pressure are too slow to be useful as an industrial tool or too complex or expensive to be used for frequent or repetitive measurements.

SUMMARY OF THE INVENTION

This invention is a method for quickly determining the vapor pressure of a hydrocarbon material, such as a petroleum product. The method of this invention quickly and inexpensively provides accurate vapor pressure data using readily available and widely used laboratory equipment whereby the method can be practiced with equipment and skills already possessed by many laboratories. The method of this invention involves performing a gas chromatogratic analysis of a sample in a special manner to produce data from which a vapor pressure can be derived.

The method of this invention preferably uses a liquid phase sample, neat or in solution, of the material the vapor pressure of which is to be measured. A suitable solvent is one that will not influence a chromatograph of the material, specifically the solvent has different volatility than any compound in the material whose vapor pressure is to be measured. Examples of suitable solvents for hydrocarbons are petroleum ether, benzene and hexane.

The sample is introduced into a gas chromatographic unit having a nonselective column and equipped with a composition detector. The sample is carried through the column with a carrier gas. A nonselective column is one that separates compounds according to boiling point rather than compound type. Materials that are more volatile require a longer column and/or a lower column temperature to obtain sharp separation.

The temperature of the column is raised according to a regular program, for example 10° C. per minute, until the desired amount of hydrocarbon vapor emerges from the column. The gas emerging from the chromatographic column is passed into a detector which is a device that measures the amounts of each component of the material relative to the amounts of the other components. The preferred detector is a hydrogen flame ionization detector. The detector produces a series of signals that usually are used to produce a strip chart but the signals from the detector may provide input to a device that is able to integrate them directly.

The various components in the sample emerge from the column in order of decreasing volatility. The detector analyzes the effluent from the column and produces a graphic representation or other record of the amount of each compound or compound group in the sample. When a graphic representation is made it is a plot of the amount of each compound or compound group versus retention time in the column and it usually appears on a calibrated strip chart as a series of peaks. The area under these peaks is proportionate to the amount of each of the compounds or compound groups in the sample. Whether a chart is produced or not, the integrated value of retention time versus quantity is referred to herein as *area*.

Prior to the analysis of the sample, the equipment is calibrated to show the positions on the record occupied by known normal paraffins. When the sample contains n-paraffins these positions appear as peaks. The vapor pressures of n-paraffins are either known or easily calculated, for example by using the Antoine equation. Calibration may be effected in a number of ways. One way is by analysis of a group of n-paraffins that are within the boiling range of the specimen to be analyzed so that the retention times of those n-paraffins are known and can be overlaid onto a strip chart or the data may be incorporated into a computer. Another way of calibrating is to incorporate a n-paraffin that is lower boiling than any portion of the sample to be analyzed so that it will produce a peak or marker on the chart that does not fall within the composition being analyzed and then to determine the positions of other n-paraffins by extrapolation. This process has good reliability.

A strip chart produced in the method of the invention will indicate the location of the n-paraffin positions or peaks. The method of the invention includes dividing the distance between consecutive n-paraffin positions in half and indicating, for example by drawing vertical lines on the chart, the points exactly between n-paraffin positions. These points are hereinafter referred as *n-paraffin bisectors*. The area between adjacent n-paraffin bisectors will have a n-paraffin position or peak occupying the center of it.

In accordance with the invention the relative area under the curve between n-paraffin bisectors is determined, for example by graphic integration in accordance with known methods. Each numerical figure for area is divided by the carbon number of the normal paraffin falling within it and this quotient is proportional to the number of moles of those compounds in the sample. The number of moles of those compounds is mathematically normalized. When the whole sample is eluted from the column it is normalized to unity and that number represents the mole fraction of the compounds in the total sample. If the whole sample is not eluted, the mole fraction between n-paraffin bisectors must be determined by other methods as described below.

The mole fraction of each area is assumed to have the vapor pressure of the normal paraffin falling within it at a given temperature, and when that mole fraction is multiplied by the known vapor pressure of the normal paraffin, the product of the multiplication is the partial pressure of that portion of the total composition. The sum of these individual partial pressures is the vapor pressure of the entire material at that temperature.

It is evident that the method of this invention is based on some approximations. One approximation is that the average vapor pressure of the compounds in the samples falling between n-paraffin bisectors is the vapor pressure of the n-paraffin between those bisectors. Another approximation is that the compounds between two n-paraffin bisectors have the same number of carbon atoms as the normal paraffin that falls between those bisectors. There are factors that compensate for and factors that diminish the significance of errors in these approximations.

Since the greatest anomolies in C number are among higher molecular weight compounds, and since high molecular weight compounds contribute relatively little to vapor pressure, these carbon number anomalies tend to have small influence on the results of an analysis.

Another factor that diminishes the effect of anomolies is that highly anomolous carbon number displacement will only be found with compositions that are greatly different in structure from n-paraffins. For example, the greatest carbon number anomoly would be expected between n-paraffins and condensed ring aromatics. However, most condensed ring aromatics are relatively high molecular weight compounds having many carbon atoms, and an error of one carbon number will be small in proportion to the total number of carbon atoms involved. For example, an error of one in a C-20 molecule is only a 5% error whereas an error of one in a C-5 molecule is a 20% error.

A compensating factor that diminishes the effect of carbon number anomalies is that compounds of different classes tend to cancel out errors. For example, aromatic compounds will normally come out of a chromatographic column near higher carbon number normal paraffins but highly branched chain hydrocarbons will normally come out near lower carbon number normal paraffins. Since a petroleum fraction will normally contain some aromatics and some highly branched paraffins, an analysis will tend to average out to the correct carbon number between n-paraffins bisectors.

Finally, as will be shown below, comparison of the method of this invention with more complex and established methods shows good correspondence.

DETAILED DESCRIPTION OF THE INVENTION

The manner in which the invention is employed is described below in conjunction with a number of vapor pressure determinations of different materials.

FIG. 1 is a reproduction of a strip chart made in accordance with this invention to determine the vapor pressure of a heavy petroleum oil.

FIG. 2 is a strip chart made in accordance with the method of this invention to determine the vapor pressure of a light petroleum oil.

FIG. 3 is a strip chart made in accordance with the method of this invention to determine the vapor pressure of a petroleum solvent.

FIG. 4 is a strip chart made in accordance with the method of this invention to determine the vapor pressure of a light petroleum solvent.

FIG. 5 is a strip chart made in accordance with the method of this invention to determine the vapor pressure of two asphalts.

The method was used to determine the vapor pressure of these different materials in order to demonstrate that the method of this invention is useful over a wide range of materials. Following are examples illustrating the method employing these different materials.

EXAMPLE 1

The vapor pressure of a heavy petroleum oil was determined. The oil was an ink oil boiling over a wide range and entirely above 260° C. An ink oil is used as a vehicle in making printing ink. The heavy oil was constituted of molecules containing more than 14 carbon atoms so n-tetradecane was used as a marker.

The sample of the heavy oil was prepared by dissolving 0.2-0.3 grams of the heavy oil in two ml of petroleum ether boiling between 20 and 40 degrees C. One drop of n-tetradecane was added to the mixture and 1-5 microliters of the solution was injected into a Varian model 1200 gas chromatograph. The column employed in the chromatograph was stainless steel, ⅛ inch in diameter and one foot long. It was filled with 5% SE30 on H/P chromosorb W, 80-100 mesh. These are products of Varian. The sample was injected into an inlet heated to 220° C. and was carried through the column with 28 ml per minute of helium and the chromatograph was recorded on a Varian model 20 strip chart recorder. The initial column temperature was 95° C. and it was raised 10° C. per minute until a temperature of 285° C. was reached.

The effluent from the chromatograph column was passed into a hydrogen flame ionization detector and the detector signal was recorded on a strip chart which is reproduced in FIG. 1. The vertical lines in FIG. 1 are the n-paraffin bisectors so that the n-paraffin positions are exactly halfway between the vertical lines. The "C" designations relate to carbon numbers of the n-paraffins, for example the designation $C_{15}$ indicates a normal paraffin having 15 carbon atoms, specifically, pentadecane.

The base line B connects the base indicating zero percent n-tetradecane to the base of the curve where no hydrocarbons are entering the hydrogen flame ionization detector. The line D is the trace made by the flame ionization detector. The area between line B and line D and between adjacent n-paraffin bisectors is proportionate to the concentration of that group of compounds in the sample.

The areas between line B and line D and between adjacent n-paraffin bisectors were graphically integrated with an instrument called a polar planimeter. An instrument such as the Supergrater, which is a programmable computing integrater produced by Columbia Scientific Industries Company could also be used. The areas between curves B and D and between each pair of n-paraffin bisectors are indicated and the values are treated as shown in Table 1 below.

TABLE 1

| C No. | Relative Area (A) | Relative Moles (A)/C No. × 100 | Mole Fraction (F) | V.P. @ 104° C., Torr. Satn. Press. (P) | Partial Press. (F) × (P) |
|---|---|---|---|---|---|
| 15 | 0.4 | 2.67 | 0.010 | 1.900 | 0.019 |
| 16 | 1.0 | 6.25 | 0.022 | 0.886 | 0.019 |
| 17 | 2.1 | 12.35 | 0.044 | 0.445 | 0.020 |
| 18 | 3.9 | 21.67 | 0.078 | 0.220 | 0.017 |
| 19 | 5.6 | 29.5 | 0.106 | 0.104 | 0.011 |
| 20 | 6.4 | 32.0 | 0.115 | 0.0349 | 0.004 |
| 21 | 7.5 | 35.7 | 0.128 | 0.0203 | 0.003 |
| 22 | 6.9 | 31.4 | 0.113 | 0.00950 | 0.001 |
| 23 | 6.2 | 27.0 | 0.097 | 0.00445 | 0.000 |
| 24 | 5.5 | 22.9 | 0.082 | 0.00209 | 0.000 |
| 25 | 4.0 | 16.0 | 0.058 | 0.00098 | 0.000 |
| 26 | 3.3 | 12.7 | 0.046 | 0.00046 | 0.000 |
| 27 | 2.8 | 10.4 | 0.037 | 0.00021 | 0.000 |
| 28–34 | 5.5 | 17.7 | 0.064 | 0.00010 | 0.000 |
|  |  | 278.2 | 1.000 | Total: | 0.094 |

In the table the column headed "C No." identifies the area in which each n-paraffin position falls, for example, the number 17 identifies the area where the n-heptadecane position falls. The column headed "Relative Area" indicates the area between lines B and D and between the n-paraffin bisectors. This area is in dimensions of volts times time and is only meaningful in this process as compared with other areas on the same strip chart, hence "Relative" Area.

The column headed "Relative Moles" is obtained by dividing the relative area by the C No. of the hydrocarbons in the area. In order to work with a convenient number, the relative moles were multiplied by 100. The values in this column are proportionate to the number of moles of the compounds represented by that area on the strip chart with respect to the number of moles of compounds represented by other areas.

The column headed "Mole Fraction" is simply the data in the Relative Moles column normalized to unity, in other words, the number in the Relative Moles column divided by the total relative moles in the sample.

The column head "Saturation Pressure" is the saturation pressure of the n-paraffin in the area involved, and these data are available from reference works such as handbooks or can be calculated using known techniques. For example, the saturation vapor pressure of n-hexadecane at 104° C. is 0.886 torr.

The column "Partial Pressure" is the product of the mole fraction and the saturation vapor pressure and is based on the principle that each compound in the composition will contribute its own partial pressure to the total vapor pressure. Finally, the total vapor pressure of the sample is obtained by adding the individual partial vapor pressures of each C No. component.

From Table 1 it is evident that at 104° C. the contribution to partial pressure of hydrocarbons having more than 22 carbon atoms is negligible in the third decimal place and can be ignored. In fact, the combined contribution of all hydrocarbons in the 28–34 carbon atom range is negligible.

Using the method of this invention the difficult task of obtaining vapor pressure of a very nonvolatile, heavy petroleum oil was easily accomplished using known laboratory manipulative techniques and readily available laboratory equipment. The vapor pressure was found to be 0.094 Torr. at 104° C. It is evident that use of calculations or handbook data to obtain the known saturation vapor pressure of the normal paraffins at any temperature can be substituted in the "Saturation Pressure" column to provide partial pressures for that temperature so that the vapor pressure of the same heavy oil at that different temperature may be obtained by mathematically manipulating the same data that were obtained from the chromatographic analysis of the specimen.

EXAMPLE 2

The vapor pressure of a petroleum base light oil was determined. The light oil boiled between 274° C. and 313° C. The light oil contained no compounds having fewer than 13 carbon atoms. The procedure for preparing the sample was the same as in Example 1 except that one drop of n-nonane was used as the n-paraffin marker and a chromatographic column ten feet long was used instead of one that was one foot long. Helium carried the sample through a column heated to 65° C. at the start of the analysis and the temperature was raised 10° C. per minute until a final temperature of 250° C. was reached. The strip chart obtained from this light oil analysis is reproduced in FIG. 2. Table 2 sets forth the data collected and the calculations made for this sample. Details of the calculations that are evident from Example 1 are omitted from Table 2. From Table 2 it is evident that the partial pressure of the specimen at 104° C. is 1.196 Torr.

TABLE 2

| C No. | Relative Area (A) | Mole Fraction (F) | V.P. @ 104° C., Torr. Satn. Press. (P) | Partial Press. (F) × (P) |
|---|---|---|---|---|
| 13 | 1.3 | 0.033 | 8.55 | 0.282 |
| 14 | 2.9 | 0.069 | 4.05 | 0.279 |
| 15 | 6.9 | 0.153 | 1.90 | 0.291 |
| 16 | 10.6 | 0.221 | 0.886 | 0.196 |
| 17 | 12.2 | 0.239 | 0.445 | 0.106 |
| 18 | 7.8 | 0.144 | 0.220 | 0.032 |
| 19 | 4.2 | 0.074 | 0.104 | 0.008 |
| 20 | 4.0 | 0.067 | 0.035 | 0.002 |
|  |  | 1.000 | Total: | 1.196 |

EXAMPLE 3

The vapor pressure of a petroleum base solvent was determined. The solvent boiled from 156°–207° C. The vapor pressure of the solvent at 20° C. was determined. The procedure set forth in Example 2 was followed except that the initial column temperature was 50° C. A position for a group of hydrocarbons boiling higher than n-octane was separately calculated. This position is designated cyclic $C_8$. The specimen was injected into the device neat rather than dissolved in a solvent. FIG. 3 is a reproduction of the strip chart that was obtained from the analysis of the specimen. Table 3 records and calculates the data from this determination. The vapor pressure of the specimen at 20° C. was determined to be 1.552 torr.

TABLE 3

| C No. | Relative Area (A) | Mole Fraction (F) | V.P. @ 20° C., Torr. Satn. Press. (P) | Partial Press. (F) × (P) |
|---|---|---|---|---|
| $C_8$ | 0.2 | 0.005 | 11.0 | 0.057 |
| cyclic $C_8$ | 1.5 | 0.039 | 7.4 | 0.290 |
| $C_9$ | 10.8 | 0.247 | 3.1 | 0.765 |

TABLE 3-continued

| | | | V.P. @ 20° C., Torr. | |
|---|---|---|---|---|
| C No. | Relative Area (A) | Mole Fraction (F) | Satn. Press. (P) | Partial Press. (F) × (P) |
| $C_{10}$ | 20.1 | 0.414 | 0.90 | 0.374 |
| $C_{11}$ | 12.5 | 0.234 | 0.26 | 0.062 |
| $C_{12}$ | 3.5 | 0.061 | 0.08 | 0.005 |
| | | 1.000 | Total: | 1.553 |

This example illustrates the flexibility of the process of this invention. To sharpen the results of this determination, the influence of the compounds designated cyclic $C_8$ was independently accounted for. This was done by assigning a saturation pressure to cyclic $C_8$ which was obtained from a plot of vapor pressure versus retention time.

EXAMPLE 4

The vapor pressure of a light petroleum base solvent boiling between 77° C. and 102° C. was determined. The vapor pressure at 20° C. was determined using the procedure of Example 3. The strip chart that was obtained in this analysis is reproduced as FIG. 4. The data set forth in Table 4 indicate further the flexibility of the method of this invention for sharpening its determinations.

TABLE 4

| | | | V.P. @ 20° C., Torr. | |
|---|---|---|---|---|
| C No. | Relative Area (A) | Mole fraction (F) | Satn. Press. (P) | Partial Press. (F) × (P) |
| br-$C_6$ | 1.0 | 0.030 | 150 | 4.50 |
| n-$C_6$ | 4.3 | 0.128 | 121.5 | 15.55 |
| cyclic $C_6$ | 3.0 | 0.089 | 96 | 8.54 |
| br-$C_7$ | 11.0 | 0.280 | 53 | 14.84 |
| n-$C_7$ | 8.9 | 0.227 | 35.6 | 8.08 |
| cyclic $C_7$ | 7.3 | 0.190 | 26.7 | 5.08 |
| br-$C_8$ | 2.0 | 0.045 | 15.5 | 0.70 |
| n-$C_8$ | 0.5 | 0.011 | 10.5 | 0.12 |
| | | 1.000 | Total: | 57.41 |

In the determination reported in Example 4, the influence on the total vapor pressure of subgroups of branched hexane, cyclic hexane, branched heptane, cyclic heptane, and branched octane are all individually accounted for. The saturation vapor pressures of these subgroups were obtained by constructing a plot relating saturation vapor pressure to retention time and then picking the saturation vapor pressure of each subgroup from the plot. The vapor pressure of this solvent at 20° C. is 57.41 torr.

EXAMPLE 5

The vapor pressures at 250° C. of two roofing asphalts were determined. It is important to know the vapor pressure of roofing asphalt at high temperature in connection with flammability specifications of roofing compositions. Both asphalts were constituted entirely of hydrocarbons having more than 16 carbon atoms per molecule so n-hexadecane was employed as a marker. This example illustrates use of the method in analyses where the sample is not completely volatilized.

The procedures for preparing and analyzing the samples were the same as in Example 1 except that a 1:1 mixture of benzene and n-hexane was used as a solvent. In order to avoid buildup of residues in the sample inlet, which might affect the results in subsequently performed tests, a freshly cleaned Pyrex injector insert was used in each analysis.

The traces from the two asphalts are illustrated on the same strip chart which is shown as FIG. 5. On FIG. 5 the line B represents no hydrocarbons, the line D is the trace made by one of the asphalts, hereinafter asphalt I, and the line E is the trace made by the other asphalt, hereinafter asphalt II.

The data obtained in the analysis for asphalt I are recorded on Table 5 and calculated as set forth below. The device employed to integrate the curves obtained from the hydrogen flame detector integrated areas between even minute intervals. To accommodate the data to the integrater a plot of n-paraffin saturation vapor pressure at 250° C. versus carbon number was made, the n-paraffin saturation vapor pressure being obtained by calculation using the Antoine equation. The data on the strip chart were integrated in one-minute intervals, and the fractional C number midway between those one-minute intervals was read from the trace. The saturation vapor pressure of the fractional C number was then obtained from the plot of saturation vapor pressure versus C number and that value was used as the saturation vapor pressure of the fractional n-paraffin. In this specification and the following claims the term *n-paraffin* shall include fractional carbon numbers.

As can be seen from Table 5, the partial pressures of hydrocarbons having more than 34 carbon atoms per molecule are so small that these hydrocarbons can be ignored in determining total vapor pressure at 250° C. Nevertheless, the molecular weight of the entire sample must be known in order to perform the calculations to determine the vapor pressure.

The quantities shown in Table 5 under the various column headings were obtained as follows.

The "Ret. Time" column gives the time at the center of each area segment measured by the integrating device at one minute intervals.

The "C No." column is a fractional carbon number obtained from a plot of the carbon number of n-paraffins versus retention time as set forth above.

The values under "Moles per 1000 g." were calculated relative to the area of the known amount of internal standard, n- hexadecane, present in the sample. These computations are conveniently made in terms of gram-atoms of carbon, which, when divided by C No., give a value for moles of hydrocarbon.

The values in the "Mole Fraction" column were computed by dividing "moles per 1000 grams" by total moles per 1000 grams of sample, which is calculated from the average molecular weight of the sample. The molecular weights of the two asphalts were determined by vapor pressure osmometry to be 646 and 669 for asphalts No. I and II, respectively.

The values in the "Satn. Press." column were obtained from a plot of carbon number of n-paraffins vs. saturation pressure which was calculated for 250° C. using the Antoine equation.

As in previous examples the partial pressures in the final column were obtained by multiplying saturation pressures by the corresponding mole fractions.

In analyzing a sample that is not completely volatilized, the process of normalizing requires determining the average molecular weight of the entire sample. When the total number of moles are known, then the mole fraction of compounds between n-paraffin bisectors can be determined. In samples in which the entire sample is volatilized, the relative moles are simply normalized to unity.

TABLE 5

| Ret. Time | C No. | Moles/ 1000 g (× 100) | Mole Fraction | V.P. @ 250° C., Torr. Satn. Press. | V.P. @ 250° C., Torr. Partial Press. |
|---|---|---|---|---|---|
| 11.5 | 22.4 | .129 | .000833 | 26.5 | .0221 |
| 12.5 | 23.6 | .345 | .00212 | 16.3 | .0346 |
| 13.5 | 24.9 | .733 | .00474 | 9.8 | .0465 |
| 14.5 | 26.3 | 0.651 | .0107 | 5.6 | .0599 |
| 15.5 | 27.7 | 3.355 | .0217 | 3.2 | .0694 |
| 16.5 | 29.1 | 5.28 | .0341 | 1.9 | .0648 |
| 17.5 | 30.6 | 6.49 | .0419 | 1.0 | .0419 |
| 18.5 | 32.4 | 6.82 | .0440 | 0.52 | .0229 |
| 19.5 | 34.3 | 6.18 | .0399 | 0.23 | .0092 |
| Total | | | .2000 | | 0.3713 |

From Table 5 it can be seen that the vapor pressure of Asphalt I is 0.3713 torr at 250° C.

TABLE 6

| Ret. Time | C No. | Moles/1000 g (×100) | Mole Fraction | 250° C. Satd. v.p., torr | Partial Press. torr |
|---|---|---|---|---|---|
| 7.5 | 18.1 | .79 | .0053 | 145 | 0.769 |
| 8.5 | 19.1 | 1.07 | .0072 | 92 | 0.662 |
| 9.5 | 20.1 | 1.62 | .0108 | 63 | 0.680 |
| 10.5 | 21.2 | 2.57 | .0172 | 42 | 0.722 |
| 11.5 | 22.4 | 3.70 | .0248 | 26.5 | 0.657 |
| 12.5 | 23.6 | 4.98 | .0333 | 16.3 | 0.543 |
| 13.5 | 24.9 | 6.21 | .0415 | 9.8 | 0.407 |
| 14.5 | 26.3 | 7.67 | .0513 | 5.6 | 0.287 |
| 15.5 | 27.7 | 9.13 | .0611 | 3.2 | 0.196 |
| 16.5 | 29.1 | 9.35 | .0626 | 1.9 | 0.119 |
| 17.5 | 30.6 | 8.40 | .0562 | 1.0 | 0.056 |
| 18.5 | 32.4 | 7.05 | .0472 | 0.52 | 0.025 |
| Total | | | .4185 | | 5.123 |

Table 6 includes the data and calculations employing the data that were obtained from the analysis of Asphalt II. From Table 6 it can be seen that the vapor pressure of Asphalt II at 250° C. is 5.123 torr.

Asphalt I and Asphalt II are similar in appearance and physical properties. The method of this invention provided an inexpensive, quick and reliable means to provide necessary flammability data that distinguishes a suitable roofing material from an unsuitable one. Although the two asphalt samples look very much alike, there is a significant difference in their saturation vapor pressures at 250° C., and Asphalt II, having a much higher vapor pressure, is a much more flammable material.

EXAMPLE 6

To establish the accuracy of the method of this invention, vapor pressure determinations were made on a number of samples both by the method of this invention and by the Reid vapor pressure method. The Reid vapor pressure method is the standard used for determining the vapor pressure of hydrocarbon mixtures in these boiling ranges. The Reid method is not suitable to determine vapor pressures below 0.1 psig and must measure vapor pressure at 37.8° C. Table 5 sets forth the data obtained in these comparative tests. In all cases, the vapor pressure reported by the method of this invention is the average of two repeated determinations and the vapor pressure reported as the Reid vapor pressure was determined by the industry-accepted method for determining vapor pressure by the Reid method.

TABLE 7

| | | Vapor Pressure (37.8° C.) | | | |
|---|---|---|---|---|---|
| Sample | Boiling Range (°F.) | Reid psig | Invention psig | Difference psig | Difference % |
| 1. Stabilized straight run Naphtha containing 8–10% Aromatics | 100–450 | 2.5 | 2.33 | −0.17 | −6.8 |
| 2. Solvent containing 98% Paraffins & Napthenes | 158–205 | 4.3 | 4.24 | −0.06 | −1.4 |
| 3. Unleaded Gasoline 30% Aromatics | 100–430 | 8.5 | 8.26 | −0.24 | −2.8 |
| 4. Light Cat-cracked Gasoline, 70% Olefins | 100–200 | 11.6 | 11.99 | +0.39 | +3.4 |

From the foregoing examples it is evident that the method of this invention provides a quick, inexpensive, and accurate method for determining the vapor pressure of hydrocarbon mixtures having widely different boiling ranges.

What is claimed is:

1. A method for determining the vapor pressure of a hydrocarbon mixture which comprises:
   a. passing a sample of said hydrocarbon mixture through a nonselective chromatographic column,
   b. analyzing the effluent from said chromatographic column in a detector,
   c. recording the signal from said detector,
   d. determining in the resultant record the location of n-paraffin positions,
   e. determining the n-paraffin bisectors at the points halfway between said n-paraffin positions,
   f. determining a base line on said record,
   g. determining the area between said base line and said record between n-paraffin bisectors,
   h. dividing each of said areas by the number of carbon atoms in the n-paraffin position falling within said area to determine the relative moles of the compounds within said areas,
   i. normalizing said relative moles to determine the mole fraction of the compounds within said area,
   j. multiplying each mole fraction thus determined by the saturation vapor pressure of the n-paraffin whose position falls within that area to determine the partial pressure of the compounds within each of said areas, and
   k. totalling said partial pressures to obtain the vapor pressure of said hydrocarbon mixture.

2. The method of claim 1 wherein said specimen is carried through said column by a gas.

3. The method of claim 2 wherein said column is heated to increasing temperatures to a final temperature that will cause substantially all of the hydrocarbons in said mixture to pass from the column.

4. The method of claim 3 wherein said column temperature is increased at a regular rate.

5. The method of claim 1 wherein said n-paraffin positions are located from a reference n-paraffin boiling at a temperature outside of the boiling range of said hydrocarbon mixture.

6. The process of claim 1 wherein positions for subgroups other than n-paraffins are located, bisectors are located between said subgroups and adjacent positions, and multiplying the mole fraction of each subgroup by the saturation vapor pressure of said subgroup.

7. The process of claim 1 wherein n-paraffin positions are at fractional carbon numbers.

* * * * *

UNITED STATES PATENT AND TRADEMARK OFFICE
CERTIFICATE OF CORRECTION

PATENT NO. : 4,366,710

DATED : January 4, 1983

INVENTOR(S) : Frank T. Eggertsen

It is certified that error appears in the above-identified patent and that said Letters Patent are hereby corrected as shown below:

Column 9, Table 5, fourth entry in column 3, delete "0.651" and insert ---1.651---.

Signed and Sealed this

Twenty-second Day of March 1983

[SEAL]

Attest:

GERALD J. MOSSINGHOFF

Attesting Officer

Commissioner of Patents and Trademarks